US00PP34712P2

(12) United States Plant Patent
Ranney et al.

(10) Patent No.: US PP34,712 P2
(45) Date of Patent: Nov. 1, 2022

(54) ***MISCANTHUS* PLANT NAMED 'NCMS3'**

(50) Latin Name: *Miscanthus sinensis*
Varietal Denomination: NCMS3

(71) Applicant: North Carolina State University, Raleigh, NC (US)

(72) Inventors: Thomas Ranney, Arden, NC (US); Darren H. Touchell, Arden, NC (US); Andra Windorf Nus, Mills River, NC (US); Irene Palmer, Mills River, NC (US); Nathan Lynch, Mills River, NC (US)

(73) Assignee: NORTH CAROLINA STATE UNIVERSITY, Raleigh, NC (US)

( * ) Notice: Subject to any disclaimer, the term of this patent is extended or adjusted under 35 U.S.C. 154(b) by 0 days.

(21) Appl. No.: 17/803,346

(22) Filed: May 24, 2022

(51) Int. Cl.
*A01H 5/12* (2018.01)
*A01H 6/46* (2018.01)

(52) U.S. Cl.
USPC ..... Plt./384

(58) Field of Classification Search
USPC ..... Plt./384
See application file for complete search history.

*Primary Examiner* — Susan McCormick Ewoldt
(74) *Attorney, Agent, or Firm* — Myers Bigel, P.A.

(57) ABSTRACT

'NCMS3' is a new cultivar of *Miscanthus sinensis* particularly distinguished by its triploid cytotype, low female fertility, and attractive variegated foliage and showy inflorescences. 'NCMS3' provides an attractive and highly infertile alternative to diploid cultivars where reseeding and naturalization is a concern.

3 Drawing Sheets

Latin name of the genus and species: The Latin name of the novel plant variety disclosed herein is *Miscanthus sinensis*.

Varietal denomination: The inventive variety of *Miscanthus sinensis* disclosed herein has been given the varietal denomination 'NCMS3'. Prior to the designation of the varietal denomination, 'NCMS3' was referred to by its experimental code: H2015-079-005.

BACKGROUND OF THE INVENTION

The present invention comprises a new and distinct cultivar of *Miscanthus*, botanically known as *Miscanthus sinensis*, and hereinafter referred to by the cultivar name 'NCMS3'. 'NCMS3' is a triploid produced from a controlled pollination. The female parent (H2011-196-001) (unpatented) was an artificially-induced tetraploid derived from seed of an open pollinated *Miscanthus sinensis* 'Zebrinus' (unpatented). The male parent was a diploid *Miscanthus sinensis* H2007-097-003 (unpatented). 'NCMS3' was first established in vitro in 2015 through embryo rescue techniques and has been asexually reproduced through micropropagation and division in Mills River, N.C. over a 6-year period. 'NCMS3' can be propagated through micropropagation or division and has been found to retain its distinctive characteristics through successive asexual propagations.

SUMMARY OF THE INVENTION

The following are the unique combination of characteristics of this new cultivar when grown under standard horticultural practices in Mills River, N.C.

'NCMS3' is a triploid *Miscanthus sinensis* with a 2C holoploid genome size of approximately 5.9 pg. 'NCMS3' is highly infertile with a 97% reduction in relative female fertility compared with the fertile diploid control, *Miscanthus sinensis* 'Zebrinus'. In addition, 'NCMS3' has upright culms and cascading variegated leaf blades resulting in an attractive form with showy inflorescences.

DESCRIPTION OF THE PHOTOGRAPHS

'NCMS3' is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *Miscanthus*.

DETAILED BOTANICAL DESCRIPTION

Figure 1:
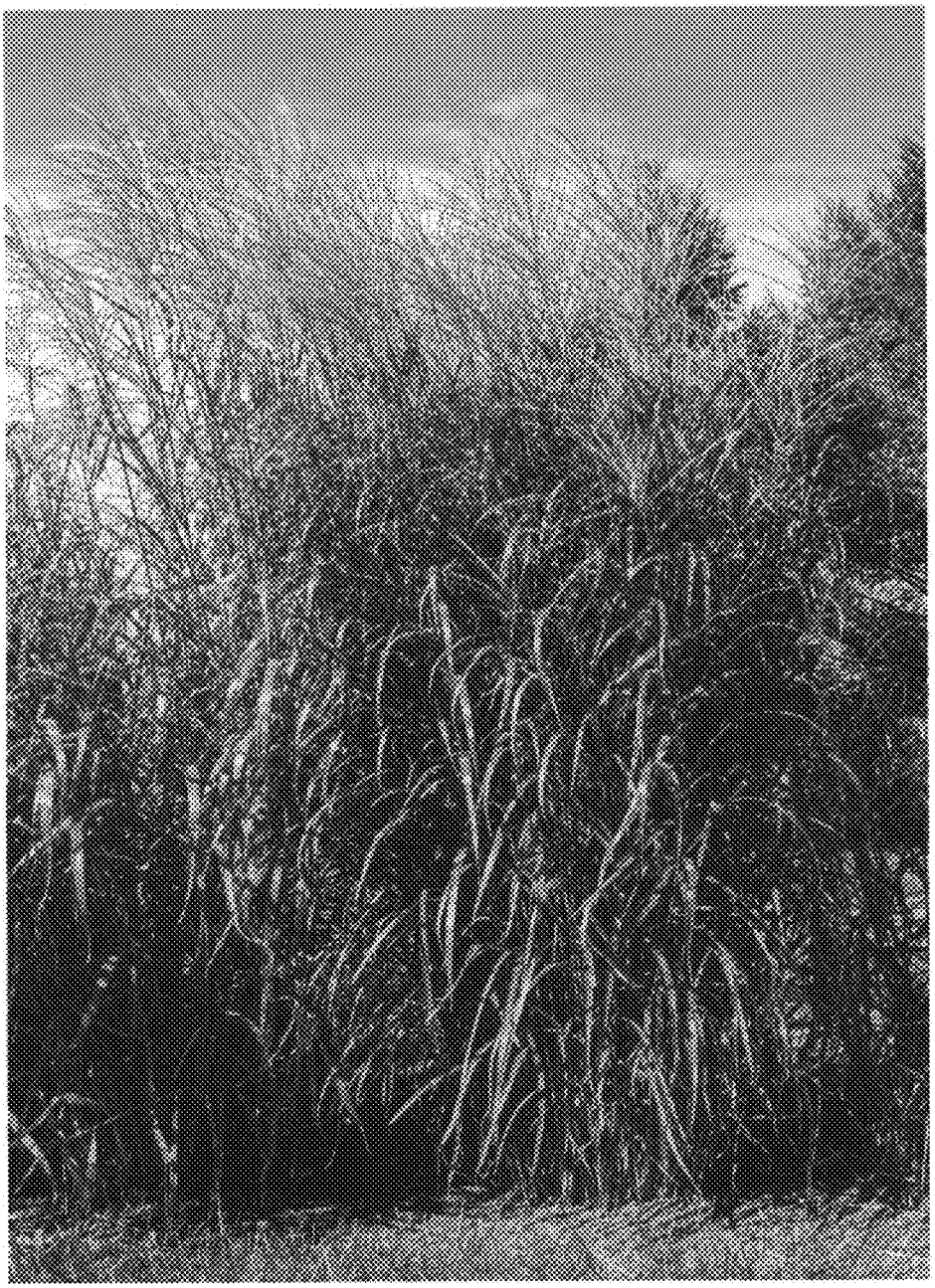
FIG. 1 is a color photograph showing the form and flowers on a 5-year-old field-grown plant of 'NCMS3' in the fall of 2021 in West Grove, Pa.
Figure 2:
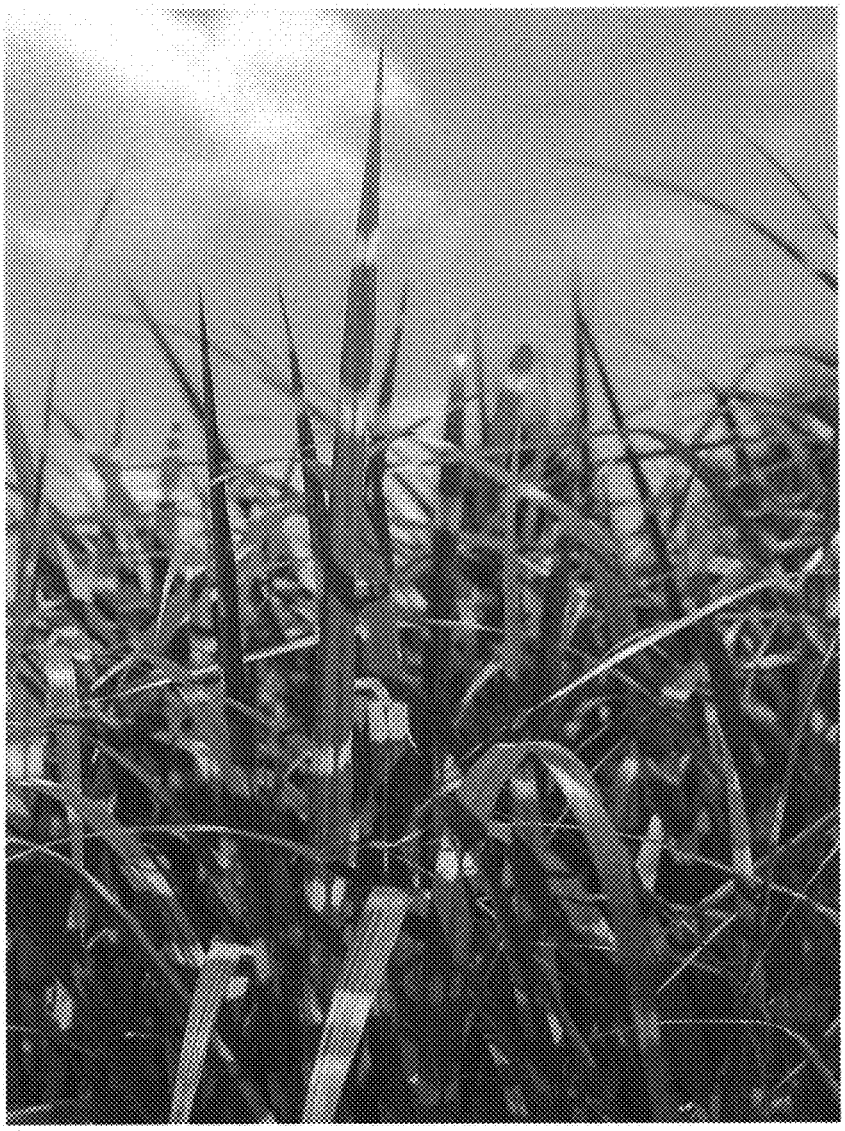
FIG. 2 is a color photograph showing a detailed view of the variegation on a 5-year-old field-grown plant of 'NCMS3' in the summer of 2021 in West Grove, Pa.
Figure 3:
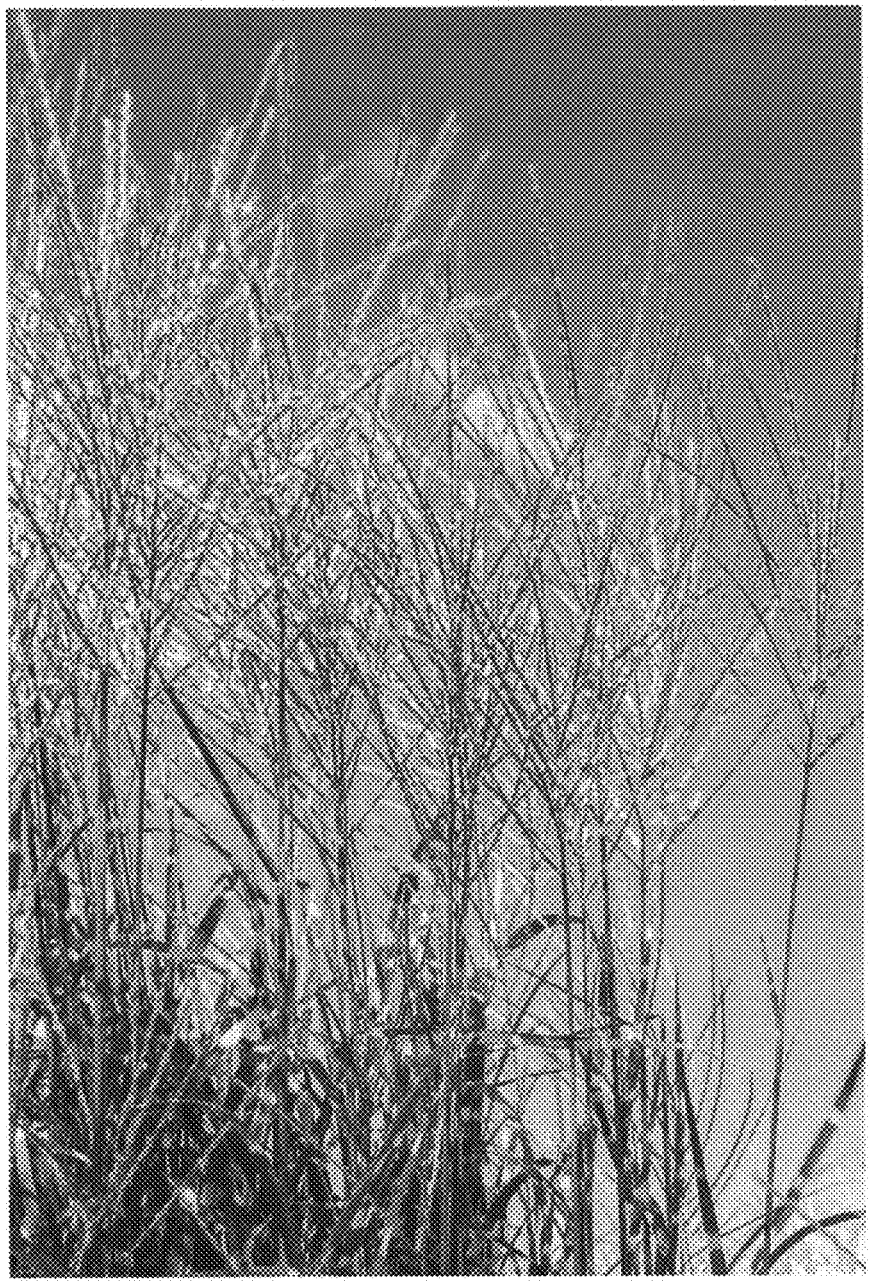
FIG. 3 is a color photograph showing a detailed view of the inflorescences of 'NCMS3' on a 5-year-old field grown plant in the fall of 2021 in West Grove, Pa.

The following is a detailed description of the botanical characteristics of the new and distinct *Miscanthus* cultivar known by the denomination 'NCMS3'. The detailed description was taken on a 4-year-old plant container-grown plant in Mills River, N.C., in 2021. All colors cited herein refer to The Royal Horticultural Society Colour Chart (The Royal Horticultural Society of London (R.H.S.), Sixth Edition). Where specific dimensions, sizes, colors and other characteristics are given, it is to be understood that such characteristics are approximations or averages set forth as accurately as possible.

Classification:

*Botanical name.*—*Miscanthus sinensis.*

*Common name.*—Maiden grass.

Parentage:

*Female parent.*—Tetraploid *Miscanthus sinensis* (H2011-196-001) derived from open-pollinated seed of *Miscanthus sinensis* 'Zebrinus'.

*Male parent.*—Diploid *Miscanthus sinensis* H2007-097-003.

Plant description:

*Growth habit.*—Clump-forming grass with upright culms and arching leaf blades.

*Mature height of foliage.*—About 125 cm to about 175 cm.

*Mature height including inflorescences.*—About 200 cm to about 225 cm.

*Mature width.*—About 100 cm.

*Average number of culms per clump.*—15.

Culms (stems):

*Shape.*—Cylindrical.

*Aspect.*—Erect and rigid, all extending from base, non-cascading.

*Mature height* (*not including inflorescence*).—About 125 to about 175 cm.

*Width.*—Avg 0.4 cm (about 0.3 cm to 0.6 cm).

*Color.*—Moderate Yellowish Green (RHS 138A).

*Texture.*—Glabrous.

*Internode length.*—Avg. 6.0 cm (about 3 cm to 15 cm).

Leaves:

*Type.*—Simple, consisting of a leaf sheath, clasping the culm, and a leaf blade, diverging from the culm at a 30-degree angle.

*Persistence.*—Leaves desiccate after freezing, but remain attached to the culm through winter.

*Arrangement.*—Alternate.

*Number.*—About 8 to about 12 per culm.

*Shape.*—Linear.

*Venation.*—Parallel with recessed midrib.

*Vein color.*—Moderate Olive Green (RHS 137B).

*Leaf sheath.*—Mature length: About 30 cm (about 20 cm to about 40 cm). Width: About 1.0 cm. Color: Moderate Olive Green (RHS 137B). Texture: Sparsely pubescent. Attachment: Leaf sheath attaches to the culm at a node. Ligule: Membrane-like tissue at the junction of the leaf sheath and leaf blade. Ligule length: About 0.2 cm. Ligule width: About 0.5 cm. Texture: Pubescent.

*Leaf blade.*—Mature leaf length: Avg. 50.0 cm about (about 20 cm to about 70 cm). Mature leaf width: Avg. 0.6 cm (about 0.3 cm to about 0.8 cm).

*Emerging leaf color.*—Upper surface: Moderate Olive Green (RHS 137B) with horizontal bands of Light Greenish Yellow (RHS 6D). Yellow bands are an average of 0.8 cm in length (0.5 to 1.0 cm), extend the width of the leaf blade and are at intervals of 2.5 cm (1 to 8 cm) along the leaf blade. Lower surface: Moderate Yellow Green (RHS 137C) with horizontal bands of Light Greenish Yellow (RHS 6D). Yellow bands are an average of 0.8 cm in length (0.5 to 1.0 cm), extend the width of the leaf blade and are at intervals of 2.5 cm (1 to 8 cm) along the leaf blade.

*Leaf color.*—Upper surface: Moderate Olive Green (RHS 137B) with horizontal bands of Light Greenish Yellow (RHS 6D). Yellow bands are an average of 0.8 cm in length (about 0.5 cm to about 1.0 cm), extend the width of the leaf blade and are at intervals of 2.5 cm (about 1 cm to about 8 cm) along the leaf blade. Lower surface: Moderate Yellow Green (RHS 137C) with horizontal bands of Light Greenish Yellow (RHS 6D). Yellow bands are an average of 0.8 cm in length (about 0.5 cm to about 1.0 cm), extend the width of the leaf blade and are at intervals of 2.5 cm (about 1 to about 8 cm) along the leaf blade.

*Winter leaf color, both upper and lower surface.*—Light Yellowish Brown (RHS 199C).

*Leaf texture.*—Pubescent.

*Leaf apex.*—Acuminate.

*Leaf margins.*—Finely serrulate.

*Leaf attachment.*—Leaf blade attaches to the leaf sheath at the ligule.

Inflorescences:

*Description.*—Terminal panicle composed of cascading racemes at anthesis.

*Flowering season.*—Late August through September in Mills River, N.C.

*Panicle.*—Number per plant: More than 50. Length: About 25 cm. Width: About 15 cm.

*Raceme.*—Number per panicle: About 25. Length: About 20 cm. Width: About 1 cm.

*Spikelet.*—Number per raceme: About 60. Length: About 0.4 cm. Width: About 0.1 cm.

*Color.*—Yellowish White (RHS 158D).

*Base.*—With fine White (RHS NN155C) hairs, about 0.7 cm in length. Awn: Length: About 0.9 cm. Width: Less than 0.1 cm.

*Lemma.*—Length: About 0.5 to 0.6 cm. Width: About 0.1 cm. Color: Light Yellow (RHS 163D).

*Palea.*—Length: About 0.4 to 0.5 cm. Width: About 0.1 cm. Color: Translucent.

*Glume.*—Length: Less than 0.4 cm. Width: Less than 0.1 cm. Color: Translucent.

*Reproductive organs.*—

*Androecium.*—Anthers: 3. Length: About 0.2 cm. Width: Less than 0.1 cm. Color: Light Yellow (RHS 162C). Pollen: Present.

*Gynoecium.*—

*Pistil.*—1.

*Stigmas.*—2.

*Length.*—About 0.2 cm.

*Width.*—Less than 0.1 cm.

*Color.*—Dark Purplish Grey (RHS N186A).

*Ovary.*—1 locule, superior.

Disease and insect resistance: No significant disease or insect pests have been observed.

Cold hardiness: At least USDA zone 5; testing has not been completed in colder zones.

Fertility: In controlled crosses under greenhouse conditions with *Miscanthus sinensis* 'Zebrinus' and 'Gracillimus' (not patented), 'NCSM3' (H2015-079-005) had greatly reduced female fertility (Table 1).

TABLE 1

Comparison of female fertility between the diploid cultivars 'Zebrinus' and 'Gracillimus' and the triploid cultivar 'NCMS3' (H2015-079-005).

| Cultivar | Seed Set (%) | Germination (%) | Overall Fertility (%) | Relative fertility (%) |
|---|---|---|---|---|
| 'Zebrinus' | 93.3 | 92 | 85.8 | 100 |
| 'Gracillimus' | 75.2 | 97 | 72.9 | 85 |
| H2015-079-005 ('NCMS3') | 7.7 | 35.6 | 2.74 | 3 |

Fertility was determined by intercrossing all three cultivars in a common greenhouse with plants arranged in a completely randomized design with 3 plant replicates per cultivar. Seed set (%) = (number of seeds/number of florets) × 100; germination (%) = (seeds germinated/total seeds) × 100; overall fertility = seed set (%) × germination (%)/100; and relative fertility = [overall fertility/85.8 (control value)]× 100.

As shown in Table 1, 'NSMS3' provides an attractive and highly infertile (97% reduction in female fertility) alternative to diploid cultivars where reseeding and naturalization is a concern. (See Rounsaville et al., 2011)

COMPARISON WITH COMMERCIAL CULTIVARS

'NCMS3' is distinguished from other cultivars as it is an autotriploid of *Miscanthus sinensis* and has reduced fertility (Table 1). In comparison to 'Zebrinus' and 'Strictus' (not patented), 'NCMS3' is triploid while 'Zebrinus' and 'Strictus' are diploid. In comparison to 'NCMS1', 'NCMS3' has variegated foliage. In comparison to 'NCMS2B', 'NCMS3' is taller with and without inflorescences.

TABLE 2

Comparison of 'NCMS3' with other *Miscanthus* cultivars.

| | 'NCMS3' | 'NCMS1' My Fair Maiden ™ (U.S. Plant Pat. No. 26,387) | 'NCMS2B' Bandwidth (U.S. Plant Pat. No. 29,460) | 'Zebrinus' | 'Strictus' |
|---|---|---|---|---|---|
| Cytotype | 3× | 3× | 3× | 2× | 2× |
| 2C relative genome size | −5.9 pg | −5.9 pg | −5.9 pg | −4.1 pg | −4.1 pg |
| Fertility | low fertility (97% reduction in female fertility compared to 'Zebrinus') | low fertility (99% reduction in female fertility compared to 'Zebrinus') | no fertile seed production observed compared to 'Zebrinus' | fertile | fertile |
| Height of foliage | 1.25 to 1.75m | 1.8 m | 0.6 to 0.9 m | 1.5 m | 1.5 m |
| Height with inflorescences | 2.0 to 2.25 m | 2.7 m | 0.9 to 1.2 m | 2.4 m | 2.4 m |
| Variegation | horizontal banding | none | horizontal banding | horizontal banding | horizontal banding |

Cytotypes and 2C relative genome size were determined folowing methods provided by Rounsaville et al., 2011.

CITATIONS

Rounsaville, T. J., D. H. Touchell, and T. G. Ranney. 2011. Fertility and reproductive pathways in diploid and triploid *Miscanthus sinensis*. Hortscience 46(10):1353-1357.

What is claimed is:

1. A new and distinct cultivar of *Miscanthus sinensis* plant named 'NCMS3' as illustrated and described herein.

* * * * *